United States Patent
Chang et al.

(10) Patent No.: US 10,656,058 B2
(45) Date of Patent: May 19, 2020

(54) BLOOD CELL AGGREGATING AGENT FOR PREPARING PARAFFIN BLOCK AND METHOD FOR PREPARING PARAFFIN BLOCK BY USING SAME

(71) Applicant: NATIONAL CANCER CENTER, Goyang-si (KR)

(72) Inventors: Hee Jin Chang, Seoul (KR); Sun Young Kim, Goyang-si (KR); Ji Yeon Baek, Goyang-si (KR); Hyun Yang Yeo, Goyang-si (KR)

(73) Assignee: NATIONAL CANCER CENTER, Goyang-si (KR)

( * ) Notice: Subject to any disclaimer, the term of this patent is extended or adjusted under 35 U.S.C. 154(b) by 549 days.

(21) Appl. No.: 14/917,687

(22) PCT Filed: Jul. 29, 2014

(86) PCT No.: PCT/KR2014/006952
§ 371 (c)(1),
(2) Date: Mar. 9, 2016

(87) PCT Pub. No.: WO2015/034178
PCT Pub. Date: Mar. 12, 2015

(65) Prior Publication Data
US 2016/0223438 A1    Aug. 4, 2016

(30) Foreign Application Priority Data

Sep. 9, 2013  (KR) .................... 10-2013-0108022
Jul. 28, 2014  (KR) .................... 10-2014-0095898

(51) Int. Cl.
*G01N 1/36*    (2006.01)
*G01N 1/28*    (2006.01)
*G01N 33/574*    (2006.01)
*C12Q 1/00*    (2006.01)
*G01N 1/30*    (2006.01)

(52) U.S. Cl.
CPC ......... *G01N 1/36* (2013.01); *G01N 33/57488* (2013.01); *G01N 1/30* (2013.01); *G01N 2001/368* (2013.01)

(58) Field of Classification Search
None
See application file for complete search history.

(56) References Cited

U.S. PATENT DOCUMENTS 3,970,427 A    7/1976  Esposito et al.
6,913,921 B2    7/2005  Fischer
(Continued)

FOREIGN PATENT DOCUMENTS

JP    2005-192521 A    7/2005
KR    1020030036010 A    5/2003
WO    WO-2012094642 A2 *    7/2012    ........ B01L 3/502761

OTHER PUBLICATIONS

Sumpelmann et al. "Haemoconcentration by gelatin-induced acceleration of erythrocytes sedimentation rate" Anaesthesia, 2000, 55, pp. 217-220. (Year: 2000).*
(Continued)

*Primary Examiner* — Blaine Lankford
*Assistant Examiner* — Lauren K Van Buren
(74) *Attorney, Agent, or Firm* — Seed Intellectual Proprety Law Group LLP

(57) ABSTRACT

The present invention relates to a material for aggregating blood cells, used in the preparation of a paraffin block for diagnosing circulating tumor cells (CTCs), and a method for preparing a paraffin block using the same, and more specifically, to a method for detecting CTCs present in the blood through blood sample collection in the preparation of a paraffin block from CTCs, which are present in a very small amount in the blood. The present invention is non-invasive and simple, and thus is very useful for the diagnosis of cancer recurrence and metastatic cancer and for prognosis (Continued)

prediction, and can be a remarkable breakthrough in cancer treatment through the analysis of the onset, metastasis and recurrence mechanisms of cancer.

6 Claims, 5 Drawing Sheets

(56) References Cited

U.S. PATENT DOCUMENTS

2005/0272103 A1* 12/2005 Chen ................ G01N 33/56966 435/7.23
2008/0070270 A1* 3/2008 Costello ............. G01N 33/5011 435/29
2010/0047860 A1* 2/2010 Fukuoka .................. G01N 1/36 435/40.52

OTHER PUBLICATIONS

Chen et al. "An improved method for generating formalin-fixed, paraffin-embedded cell blocks" Journal of histotechnology 35(2) Jul. 2012 (Year: 2012).*

Brown et al., "Gelatin-Embedded Cell-Polymer Constructs for Histological Cryosectioning," *J Biomed Mater Res. Part B: Appl Biomater.* 72B:79-85 (2005).

Chen et al., "An improved method for generating formalin-fixed, paraffin-embedded cell blocks," *Journal of Histotechnology* 35(1):11-16 (2012).

* cited by examiner

[Figure 1]
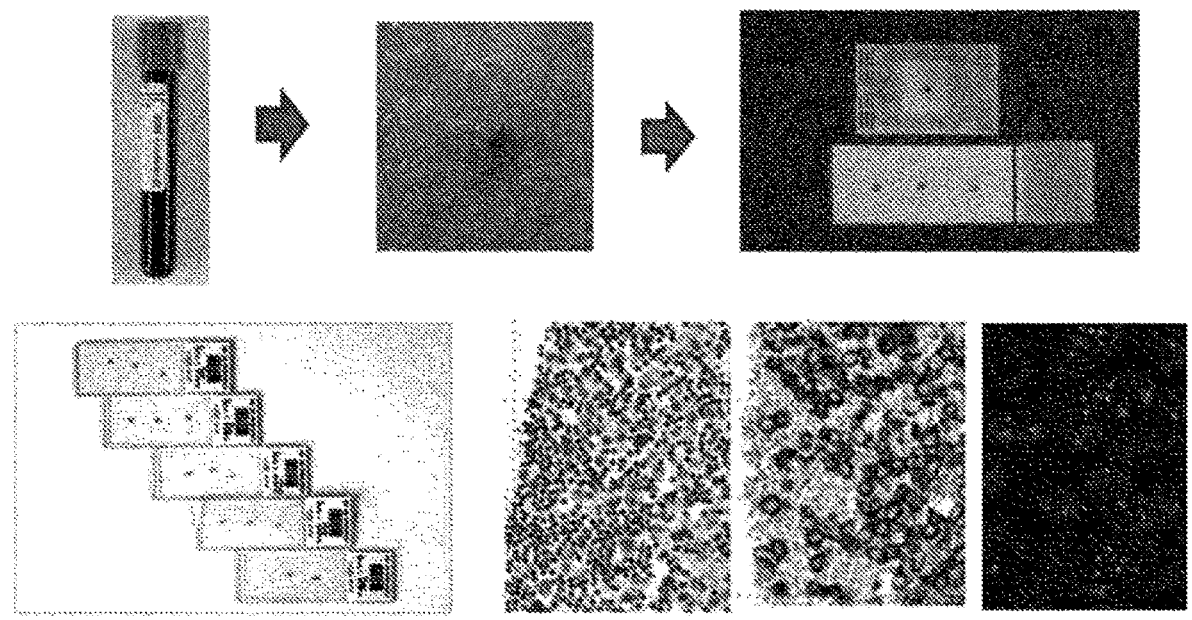
[Figure 2]
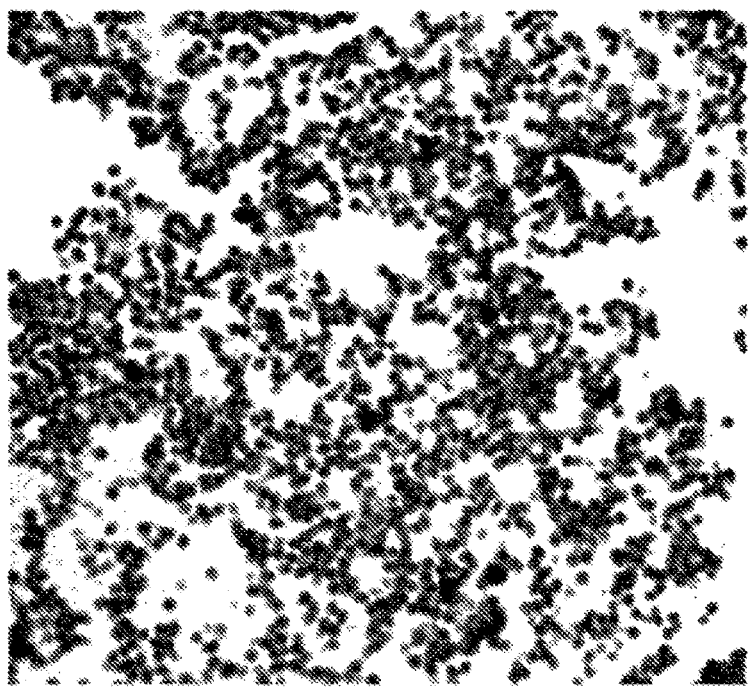

[Figure 3]
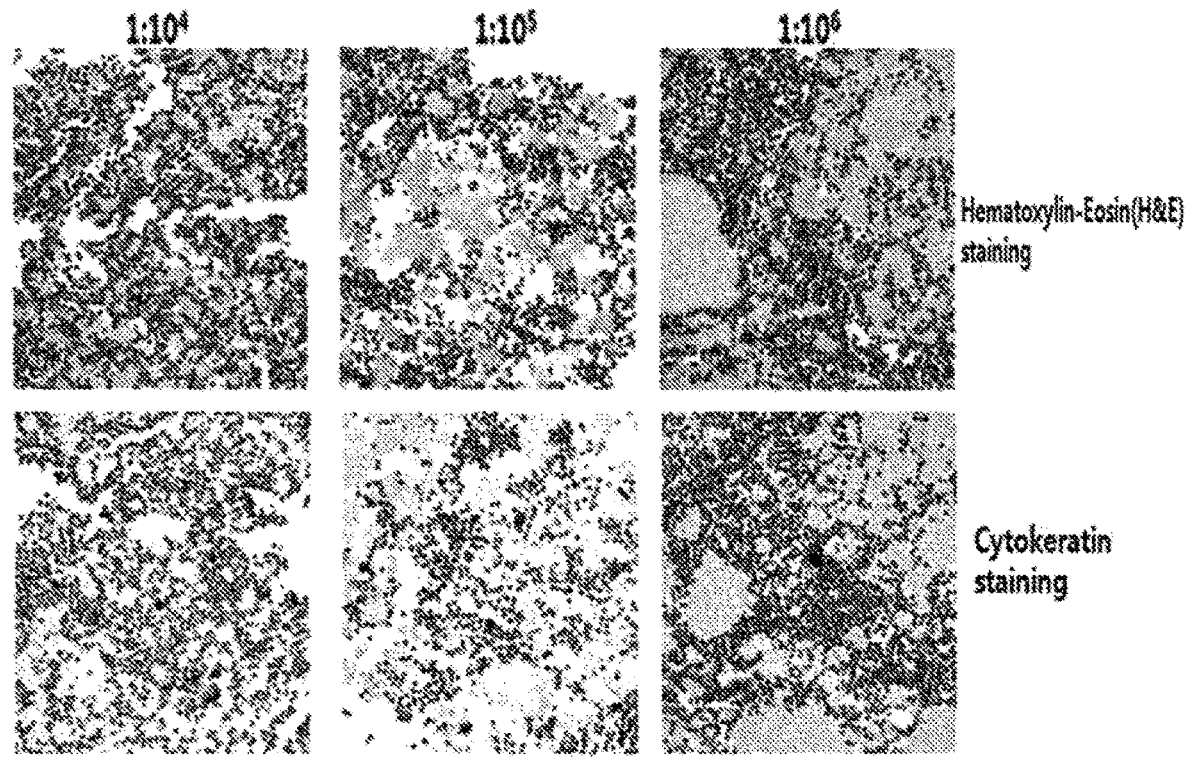
[Figure 4]
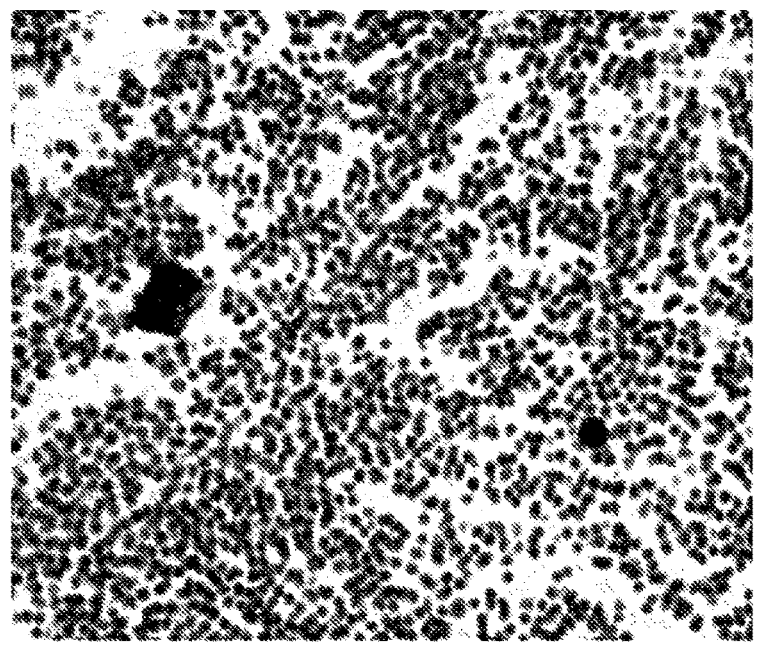

[Figure 5]
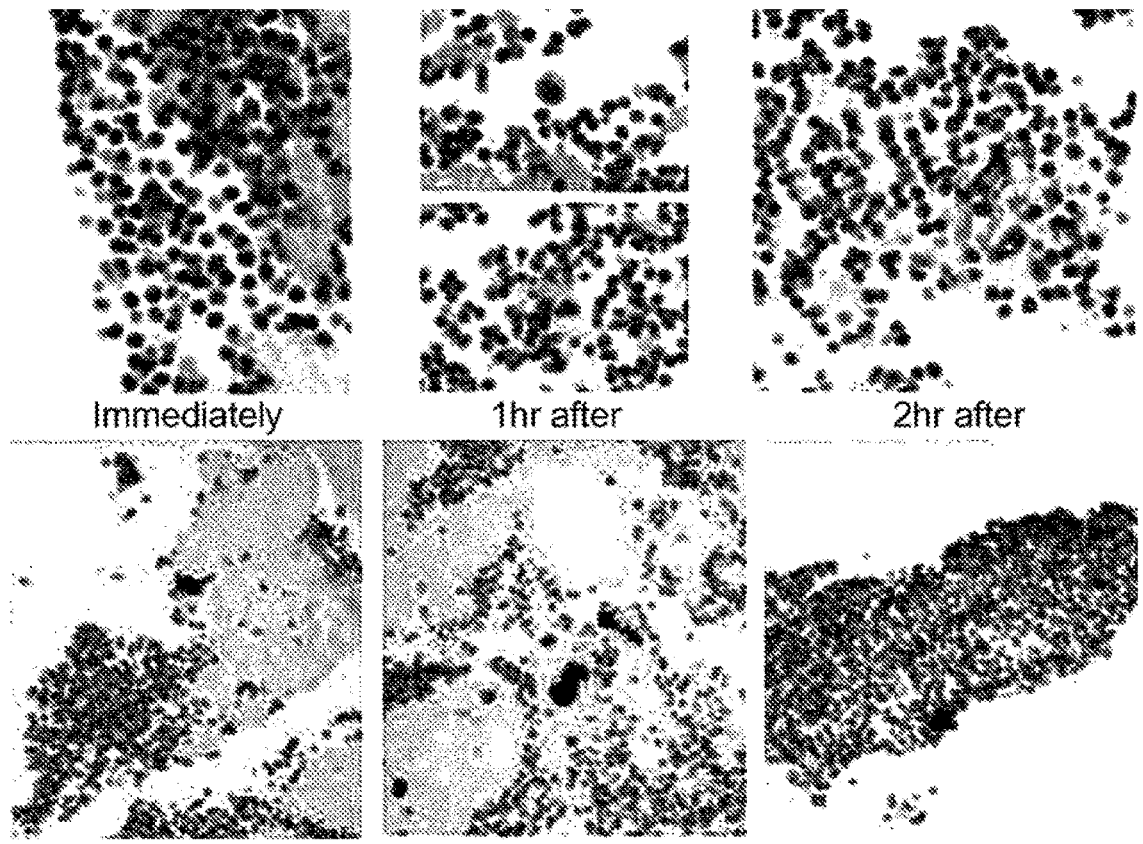
[Figure 6]
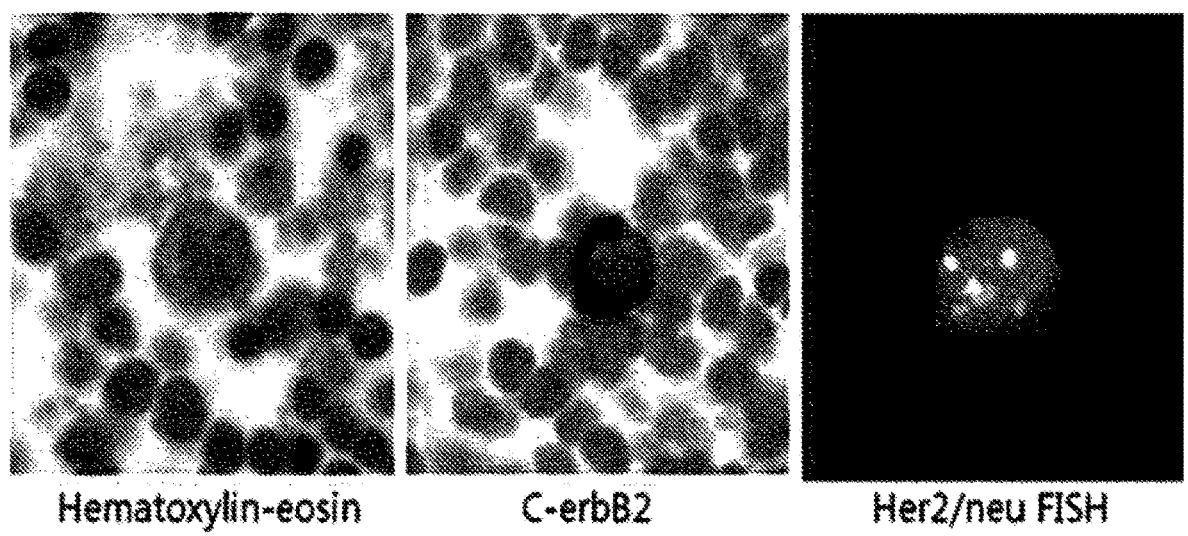

[Figure 7]
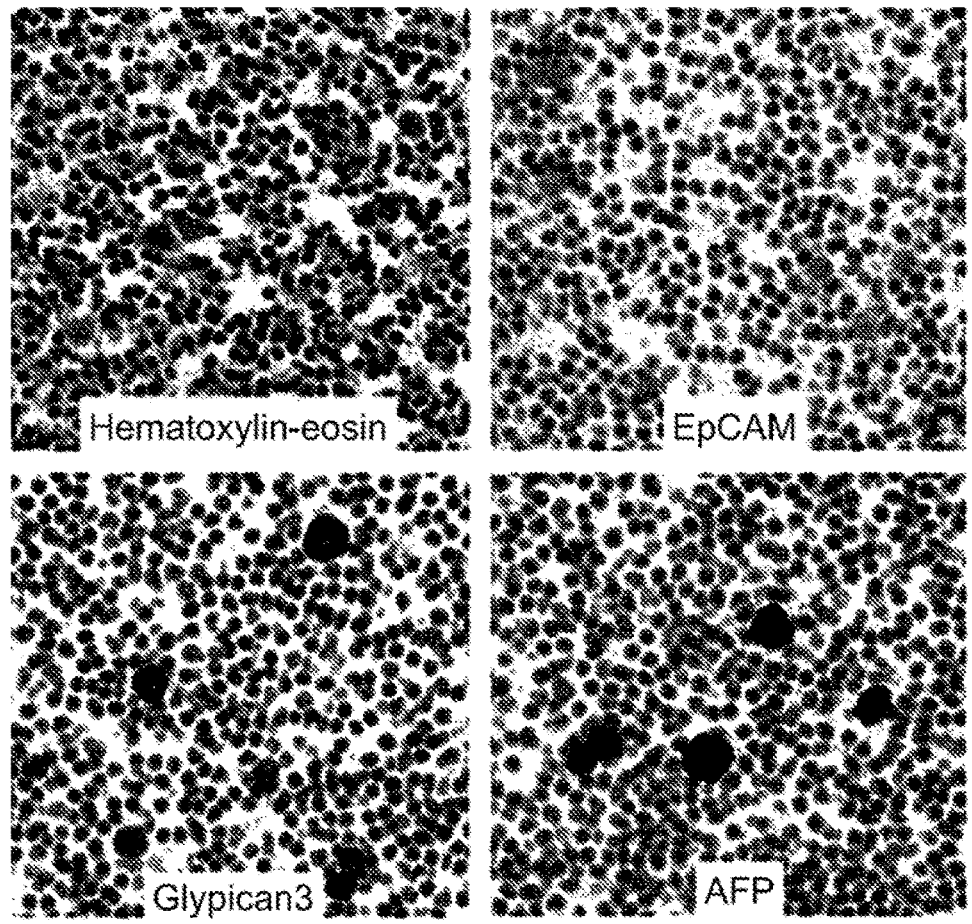
[Figure 8]
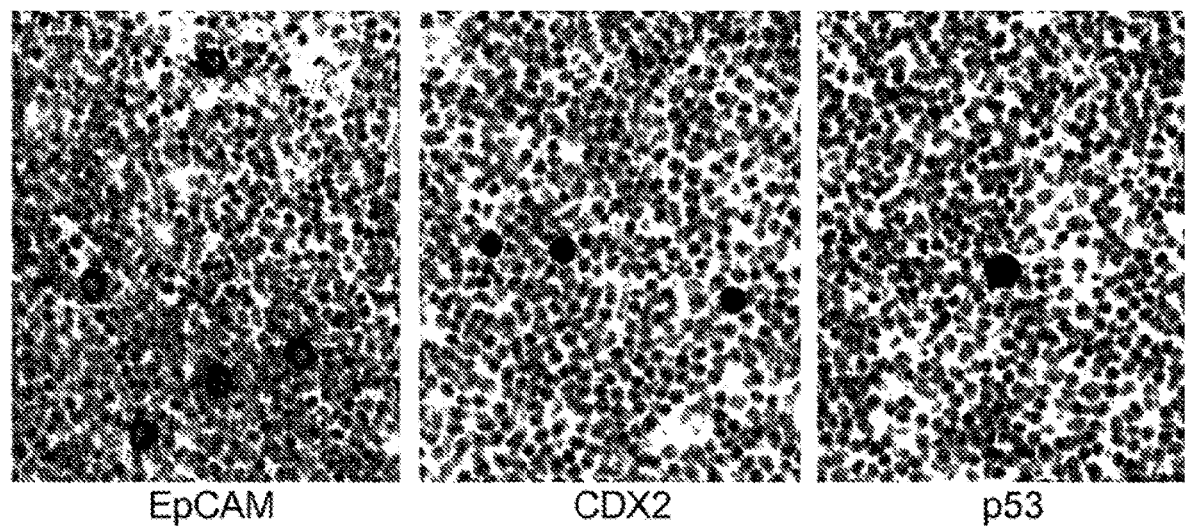

[Figure 9]
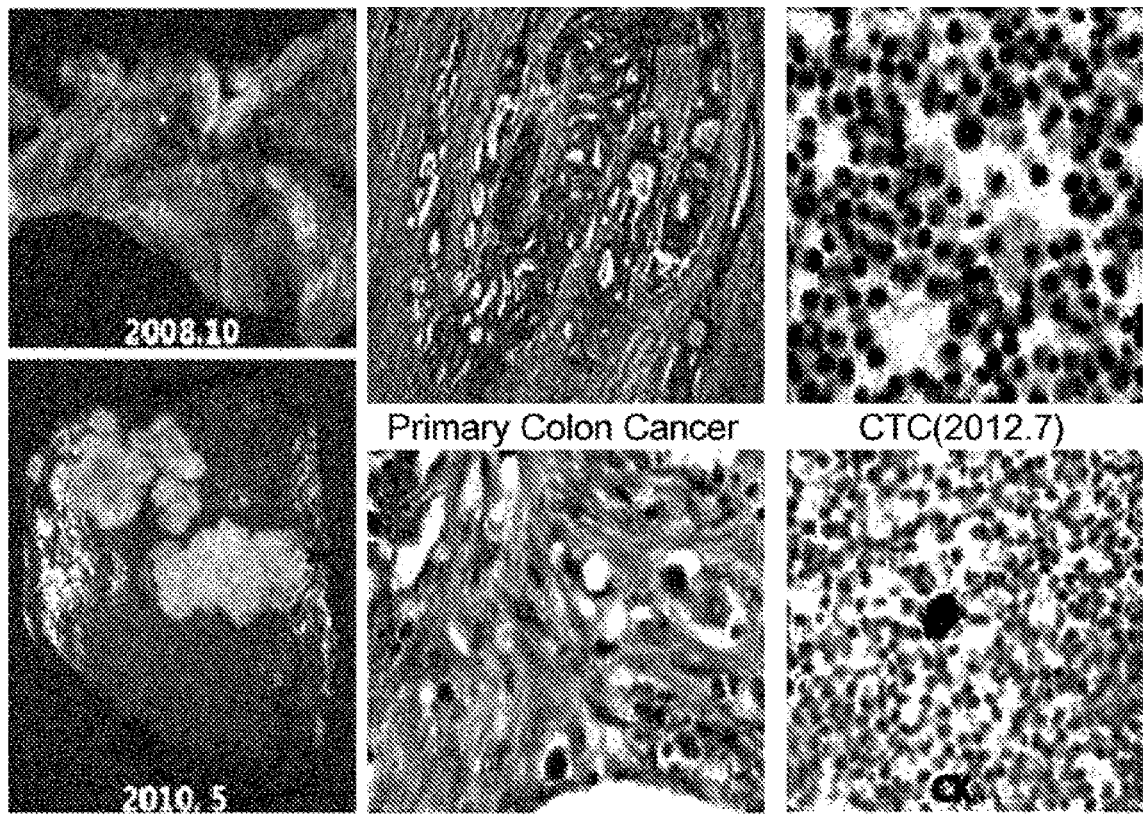
[Figure 10]
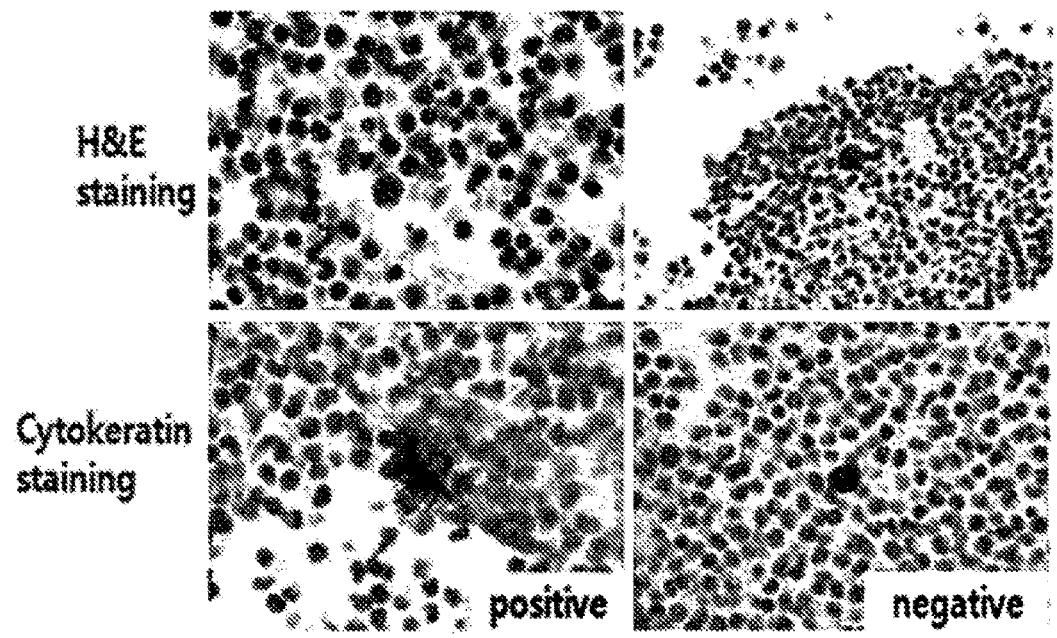

BLOOD CELL AGGREGATING AGENT FOR PREPARING PARAFFIN BLOCK AND METHOD FOR PREPARING PARAFFIN BLOCK BY USING SAME

TECHNICAL FIELD

The present invention relates to a blood cell aggregating agent and a method for preparing a paraffin block using the same. More specifically, the present invention, in preparing a paraffin block including blood cells present in the blood free of red blood cells from a small amount of blood, relates to a blood cell aggregating agent which can improve the aggregating property of blood cells and at the same time significantly prevent the damage and loss of blood cells thus capable of providing a paraffin block with high reproducibility, excellent sensitivity and specificity for the diagnosis of circulating tumor cells, and a method of preparing a paraffin block using the same.

BACKGROUND ART

Circulating tumor cells (hereinafter; CTC) are rare tumor cells present in the blood and circulate through the body, and are known to be present at a rate of 1/1,0000,000 blood cells of a cancer patient. Despite the presence of only an extremely small amount in the blood, the presence of CTCs has been known as an important factor for the prognosis associated with survival rate in patients with metastatic breast cancer, colorectal cancer, and prostate cancer. Recently, there were reports that therapeutic responses can be easily predicted by monitoring tumor-specific markers of CTCs in the blood.

In the conventional diagnosis of cancer using blood, the prognosis of cancer occurrence was predicted based on the increase in expression of particular enzymes, etc., and Korean Patent Application Publication No. 2003-0036010 discloses a method for cancer diagnosis by measurement of enzyme activity of protein kinase in the blood.

However, until now, the detection of CTCs in the blood, which are not particular enzymes, has been mostly limited to the quantitative analysis of estimating the amount of tumor cells in the blood, i.e., the degree of tumor burden. If it is possible to collect the detected CTCs and analyze them pathologically, the method will be able to replace the performance of a histological examination for patients with terminal cancer, who have difficulty in receiving histological examination, reduce expenses for unnecessary examination, and indirectly reduce the cost for treatment by performing appropriate treatments suitable for the histological type of cancer, and thus the study has been continued.

Examples of the representative methods known so far by such study include an immunological assay using monoclonal antibodies and a separation method according to cell size, which are at the early stage of development and are partially commercialized. However, the method used at present is a test method for a one-time use, which only enables a simple count of CTCs or one or two times of immunocytochemical staining regarding the CTCs. Additionally, the immunological assay has a disadvantage in that, in the case of CTCs, hepatocellular carcinoma or malignant melanoma which exhibits an epithelial-mesenchymal transition (EMT), false-negatives may appear because the markers may not respond to cancer cells. Furthermore, the separation method according to cell size, which collects CTCs using a micro filter membrane with pores, has disadvantages in that the method, for lacking the variety in pore size, cannot filter the cancer cells which are smaller than the pores in the micro filter membrane, whereas the pore size may be clogged by the aggregation of white blood cells. Accordingly, both methods have fatal problems.

Additionally, the convention method of diagnosis was to extract only CTCs by removing red blood cells by chemical treatment followed by removing white blood cells by micro filtration method or surface markers, which required many steps before extracting the final CTCs, thus having a problem of reducing recovery rate of CTCs.

As a method of resolving the above problem, the CTCs may be detected using paraffin blocks which include circulating tumor cells.

Conventionally, paraffin blocks are being used to figure out the shapes of cells or tissues and, based on the results, use them for the diagnosis, treatment, and research of diseases via special staining, immunohistochemical staining, etc. The application of the paraffin blocks are generally performed using biopsy specimens. Upon fixation, the tissues go through with a process of washing, dehydration, clearing, and paraffin penetration to prepare paraffin blocks, which are then cut into a predetermined thickness and dried.

For the application of the paraffin blocks into blood cells, the blood cells should be fixed in a fixing solution to prepare cell blocks and then prepared into blood sections. In particular, examples of the conventional methods of preparing cell blocks for the biopsy specimens include: a) a fixed sediment method, in which centrifuged sediment is fixed in formalin; b) an egg-albumin method, which employs the principle that egg-albumin is agglutinated in ethanol; c) an agar method; d) a plasma thrombin clot method; e) collodion bag method; f) Millpore filter method, etc.

However, when an agar gel is used for the preparation of the cell blocks among the conventional methods, it has a problem in that the agar gel which supports the specimen, and thus significantly increase the time required for the preparation of paraffin blocks and the cost involved thereof thereby not being able to obtain satisfied results.

Additionally, when the fixed sediment method which precipitates specimens via centrifugation is used for the blood cells among the conventional methods, it has problems in that the amount of the cell block becomes smaller or the cells or tissues become spread due to the destruction and loss of the blood cells, and it becomes difficult to distinguish the cell block from paraffin after paraffin penetration, and it is impossible to embed using a forceps during the embedding process.

Additionally, when the paraffin block specimens prepared using the blood cells into cell blocks using the conventional methods are stained, it is difficult to perform a slide reading due to the background staining, and also there is a problem in that the sensitivity and specificity for the detection of targeted particular blood cells deteriorate due to the destruction and loss of the blood cells.

Furthermore, the subjects of diagnosis using the paraffin blocks are the conventional biopsy specimens or body cells, and these biopsy specimens or body cells have good intercellular adhesion and contain extracellular matrix components which aggregate cells, and thus were easy for preparing cell blocks. However, blood cells neither have the intercellular adhesion nor contain the extracellular matrix components which aggregate cells, and thus they are in a separate state without being aggregated. The blood cell sample in this state cannot allow the blood cells to aggregate, and thus regardless of the use of various methods for preparing cell blocks described above, the blood cells would not be aggregated. Accordingly, when paraffin blocks are prepared for the blood cells, the vanishing or loss of the blood cells during the preparation process may frequently occur thus making it difficult to prepare the intended paraffin blocks.

Even furthermore, when blood cells are subjected to the process of formalin fixation or paraffin block preparation without being properly aggregated, the blood cells themselves may be unprotected by being exposed to the outside, and thus the destruction, vanishing, or loss may occur more frequently. In particular, the CTCs, although included in the blood, are contained in an extremely small number. Therefore, when the blood cells being destroyed, vanished, or lost are the CTCs, it can cause a fatal problem in that CTCs cannot be diagnosed via the prepared paraffin blocks.

DISCLOSURE OF THE INVENTION

Technical Problem

The present invention has been contrived for obviating the problems described above, and the first object of the present invention is to provide a blood cell aggregating agent which can improve the reliability of diagnosis of the intended particular blood cells by facilitating the preparation of paraffin blocks and preventing the destruction, damage, vanishing, loss, etc., during the preparation process.

The second object of the present invention is to provide a diagnostic kit for CTCs with excellent reproducibility, sensitivity, and specificity, in diagnosing CTCs.

The third object of the present invention is to provide a method for preparing paraffin blocks using the blood cell aggregating agent with significantly excellent reproducibility, sensitivity, and specificity.

Technical Solution

To achieve the first object, the present invention provides a blood cell aggregating agent for preparing a paraffin block, including a material for aggregating blood cells, which performs the functions of extracellular matrix to aggregate blood cells and prevent damage and loss of blood cells.

According to an exemplary embodiment of the present invention, the material for aggregating blood cells may contain gelatin.

According to another exemplary embodiment of the present invention, the gelatin concentration in the aggregating agent may be in a range from 5 mg/mL to 35 mg/mL.

According to still another exemplary embodiment of the present invention, the material for aggregating blood cells further may include at least one material selected from the group consisting of pectin, chondroitin sulfate, fibronectin, starch, and laminin.

According to still another exemplary embodiment of the present invention, the material, which is further added as the material for aggregating blood cells in addition to gelatin, may be contained in an amount of 5 wt % or less relative to the weight of gelatin.

According to still another exemplary embodiment of the present invention, the blood cell aggregating agent further may include a color fixing agent for color development of the material for aggregating blood cells, and the color fixing agent may be contained in an amount from 5 volume parts to 10 volume parts relative to 100 volume parts of the material for aggregating blood cells.

According to still another exemplary embodiment of the present invention, the gelatin concentration may be in a range from 10 mg/mL to 30 mg/mL.

According to still another exemplary embodiment of the present invention, the blood cell aggregating agent may be used for the diagnosis of CTCs.

Additionally, to achieve the second object of the present invention, the present invention provides a diagnostic kit for CTCs including the blood cell aggregating agent for the preparation of the paraffin blocks according to the present invention.

Additionally, to achieve the third object of the present invention, the present invention provides a method of preparing a paraffin block using a blood cell aggregating agent, including: (1) removing red blood cells from a subject and extracting blood cells therefrom; (2) mixing the blood cells with the blood cell aggregating agent of claim 1 to prepare blood cell aggregates; (3) curing the blood cell aggregates; and (4) treating the paraffin block forming material on the cured product according to step (3).

According to an exemplary embodiment of the present invention, the tube used in step (1) into which the blood cells are extracted may be coated with a gelatin solution.

According to another exemplary embodiment of the present invention, the removing of red blood cells may be performed using Ficoll.

According to still another exemplary embodiment of the present invention, in step (2), the blood cells and the blood cell aggregating agent may be mixed in a volume ratio of 1:1 to 1.5.

According to still another exemplary embodiment of the present invention, the blood cell aggregating agent in step (2) may include gelatin, and the gelatin concentration in the blood cell aggregating agent may satisfy, according to the temperature at which step (2) is performed, any one of the conditions from (a) to (c).

(a) The gelatin concentration in the blood cell aggregating agent may be in a range from 5 mg/mL to 15 mg/mL, when step (2) is performed at a temperature between 5° C. or higher and lower than 15° C.; (b) the gelatin concentration in the blood cell aggregating agent may be in a range from 15 mg/mL to 25 mg/mL, when step (2) is performed at a temperature between 15° C. or higher and lower than 25° C.; and (c) the gelatin concentration in the blood cell aggregating agent may be in a range from 25 mg/mL to 35 mg/mL, when step (2) is performed at a temperature between higher than 25° C. and lower than 35° C.

According to still another exemplary embodiment of the present invention, the paraffin block forming material in step (4) may include alcohol, xylene, and paraffin; and step (4) may be performed via autopenetration process by sequentially treating the paraffin block forming material with alcohol, xylene, and paraffin in this order.

According to still another exemplary embodiment of the present invention, the paraffin block may be used for histological, immunohistochemical, or molecular biological detection methods of circulating tumor cells.

According to still another exemplary embodiment of the present invention, the method may further include a step of fixing the cured product according to step (3) after step (3).

According to still another exemplary embodiment of the present invention, the fixation of the cured product may be performed using at least one kind selected from the group consisting of formalin, methanol, and ethanol.

Hereinafter, the terms used in the present invention are defined.

As used herein, the term "blood cells" preferably refers to cells included in the peripheral blood, and the blood cell includes both nucleated cells and anucleated cells, and the blood cells also include normal cells and/or cancer cells in addition to the conventional blood cells, and the blood cells refer to all the cells including macrophages, lymphocytes, peripheral blood mononuclear cells (PBMC) such as monocytes, red blood cells, white blood cells, platelets, etc., which are conventionally classified as blood cells.

Advantageous Effects

The present invention can solve the difficulties present in the conventional methods in preparing cell blocks in the fixation of blood cells during the process of preparing paraffin blocks; and also the fatal problems occurring in the conventional methods during the process of preparing cell blocks of blood cells into paraffin blocks such as damage, loss and/or vanishing. By doing so, the particular target cells in the blood cells can be included in the paraffin blocks without damage, loss, and/or vanishing, and thus the targeted particular cells, e.g., CTCs, can be detected using the paraffin blocks via various methods such as histological, immunohistochemical, and molecular biological methods.

Additionally, the method of the present invention does not require performing several times of centrifugation of the blood cells, thus enabling to simplify the preparation process of paraffin blocks, and as a result, capable of reducing the time required for preparation and the production cost.

Additionally, the method of the present invention can omit the physical or chemical treatment process such as the method of removing white blood cells via micro filtration method or surface marker, after removing red blood cells from the blood as in the conventional method of detecting CTCs, thus capable of reducing the loss of the target CTCs while improving cell preservation rate.

Furthermore, the paraffin blocks including blood cells prepared in the present invention can reduce the background staining, obtain thin specimens, thus enabling to provide excellent resolution. Additionally, the paraffin blocks of the present invention can provide a morphological confirmation of CTCs, and thus distinguish from contaminated epithelial cells, and as a result, reduce the determination of false-positives thereby providing extremely excellent sensitivity and specificity. Furthermore, the number of CTCs per unit volume can be counted by counting the number of white blood cells and CTCs included in the unit area. Even furthermore, since the biopsy specimens can be prepared in paraffin blocks they can be stored permanently, and can perform at least 30 times of various immunohistochemical tests. Moreover, since paraffin blocks can be prepared by collecting a small amount of blood, the blood collected from a subject to be tested at time intervals can be prepared into paraffin blocks and used in tests, for the diagnosis of cancer recurrence, metastasis, and prognosis.

BRIEF DESCRIPTION OF THE DRAWINGS

FIG. 1 shows a schematic experimental process regarding the method of preparing a paraffin block according to an exemplary embodiment of the present invention.

FIG. 2 shows a picture of a paraffin section prepared from a circulating tumor cell derived from a colorectal cancer cell line (SW620) according to an exemplary embodiment of the present invention, observed under a microscope with 200× magnification after cytokeratin (CK) immunohistochemical staining.

FIG. 3 shows pictures of paraffin sections prepared by spiking the CTCs derived from a colorectal cancer cell line (SW620) in normal blood by varying the ratio between cancer cells:white blood cells according to an exemplary embodiment, observed under a microscope with 200× magnification after performing H & E staining and CK immunohistochemical staining.

FIG. 4 shows a picture of a paraffin section prepared from a circulating tumor cell derived from a colorectal cancer cell line (SW620) according to an exemplary embodiment of the present invention, observed of the detection of false-positives due to contamination under a microscope with 400× magnification after CK immunohistochemical staining.

FIG. 5 shows pictures illustrating the cytological features of the CTCs observed under a microscope through paraffin blocks, which were prepared by placing the blood specimens derived from a breast cancer cell line (SKBR3) according to time from the blood collection to separation of red blood cells, according to an exemplary embodiment of the present invention.

FIG. 6 shows pictures of paraffin block sections prepared from the CTCs derived from a breast cancer cell line (SKBR3) according to an exemplary embodiment of the present invention, observed under a microscope with 1000× magnification after performing H & E staining, c-erbB2 immunohistochemical staining, and fluorescence in situ hybridization (FISH) for Her2/neu gene.

FIG. 7 shows pictures of paraffin sections prepared from the CTCs derived from a liver cancer cell line (HepG2) according to an exemplary embodiment of the present invention, observed of the gene expression of a cancer-specific marker (EpCAM) and liver cancer-specific markers (Glypican-3 and alpha-fetoprotein (AFP) under a microscope with 400× magnification after performing H&E staining and CK immunohistochemical staining.

FIG. 8 shows pictures of paraffin sections prepared from the CTCs derived from a colorectal cancer cell line (SW620) according to an exemplary embodiment of the present invention, observed of the gene expression of a cancer-specific marker (EpCAM) and colorectal cancer-specific markers (CDX2 and p53) under a microscope with 400× magnification after performing CK immunohistochemical staining.

FIG. 9 shows pictures of paraffin sections prepared from the blood of a patient with colorectal cancer stage 4 with liver metastasis according to an exemplary embodiment of the present invention, observed of the cytological features of the cancer cells of primary tumor and CTCs under a microscope with 400× magnification after performing H & E staining and CK immunohistochemical staining.

FIG. 10 shows pictures of CTCs observed in the blood of the above patient, observed under a microscope with 400× magnification after performing H & E staining and CK immunohistochemical staining.

BEST MODE FOR CARRYING OUT THE INVENTION

Hereinafter, the present invention will be explained in further details.

As described above, although paraffin blocks are being used for figuring out the shapes of cells or tissues and, based on the results, use them for the diagnosis, treatment, and research of diseases via special staining, immunohistochemical staining, etc, the conventional methods had much difficulty in preparing paraffin blocks from the blood cells. Additionally, even when paraffin blocks are prepared by converting the blood cells into cell blocks using the conventional methods, the staining of the paraffin block results in excessive background staining thus significantly deteriorating the sensitivity and specificity required for the detection of targeted particular blood cells. Furthermore, since the blood cells, unlike the biopsy specimens, do not contain the materials which perform the functions of extracellular matrix such as intercellular aggregation on the surface of cell membrane, and thus each cell becomes separated instead of being aggregated, thus causing frequent vanishing or loss of blood cells during the preparation of paraffin blocks, and making the preparation of paraffin blocks very difficult. Even furthermore, when blood cells are subjected to the process of formalin fixation or paraffin block preparation, the blood cells themselves are not protected by being exposed to the outside, and thus the destruction, vanishing, and/or loss of the blood cells occurred frequently during the various intermediate processes of preparing paraffin blocks. In particular, the CTCs, although included in the blood, are contained in an extremely small number. Therefore, when the blood cells being destroyed, vanished, or lost are the CTCs, it had a fatal problem in that CTCs could not be diagnosed using the prepared paraffin blocks. Additionally, the convention method of diagnosis was to extract only CTCs by removing red blood cells by chemical treatment followed by removing white blood cells by micro filtration method or surface markers, which required many steps before extracting the final CTCs, thus having a problem of reducing the recovery rate of CTCs.

In this regard, in the present invention, an attempt was made to solve the above problems using a blood cell aggregating agent for preparing paraffin blocks including a material for aggregating blood cells, which perform the functions of extracellular matrix to aggregate blood cells and prevent damage and loss of blood cells. In preparing paraffin blocks including the blood cells as such, the difficulty of the conventional methods in preparing the blood cells into cell blocks using the conventional biopsy specimens, and the fatal problem of the conventional methods in that the cell blocks prepared according to the standardized method of biopsy specimens are damaged, lost, and/or vanished during the process of paraffin block preparation can be resolved. By doing so, the particular target cells in the blood cells can be included in the paraffin blocks without damage, loss, and/or vanishing, and thus the targeted particular cells, e.g., CTCs, can be detected using the paraffin blocks via various methods such as histological, immunohistochemical, and molecular biological methods. Additionally, the method does not require performing several times of centrifugation of the blood cells, thus enabling to simplify the preparation process of paraffin blocks, and as a result, reducing the time required for preparation and the production cost. Furthermore, the method of the present invention can omit the multi-step physical or chemical treatment process for removing blood cells as in the conventional detection method of CTCs, thus capable of reducing the loss of the target CTCs while improving cell preservation rate.

First, the material for aggregating blood cells which performs the functions of extracellular matrix to aggregate blood cells and prevent damage and loss of the blood cells will be explained.

Specifically, the blood cells refer to the cells included in the blood, preferably in the peripheral blood, and the blood cells may include both nucleated cells and anucleated cells, and the blood cells may include the conventional blood cells, normal cells and/or cancer cells, and the blood cells refer to all the cells including macrophages, lymphocytes, peripheral blood mononuclear cells (PBMC) such as monocytes, red blood cells, white blood cells, platelets, etc., which are conventionally classified as blood cells.

Preferably, the material for aggregating blood cells can perform the functions of extracellular matrix for the blood cells in which red blood cells were removed. The material for aggregating blood cells according to the present invention may not vary the degree of exhibiting effects according to the specific types of the blood cells. However, when the paraffin blocks are prepared for the diagnosis of particular blood cells other than red blood cells among the blood cells, e.g., CTCs, the material for aggregating blood cells according to the present invention may be able to perform the functions of the extracellular matrix for the cells free of red blood cells form the blood cells. Conventionally, since the red blood cells among the CTCs included in the blood account for high percentage in number, when paraffin blocks are prepared to include red blood cells, the probability that the targeted particular type of blood cells can be included in the blood cells, which are to be included per unit area of the thus-prepared paraffin block sections, may be very low. Additionally, when red blood cells are damaged or destroyed during the process of paraffin block preparation, various kinds of enzymes that may affect the cell membranes, DNA, RNA, cytoplasm, etc., of particular types of blood cells may be released, thus making the diagnosis of the targeted particular blood cells very disadvantageous or impossible. Accordingly, in preparing paraffin blocks for the diagnosis of CTCs, it is preferable that the material for aggregating blood cells perform the functions of the extracellular matrix on the blood cells free of red blood cells.

Meanwhile, the material for aggregating blood cells performs the functions of aggregating blood cells and preventing the damage and loss of blood cells. The functions of the material for aggregating blood cells will be described in more details herein below.

Conventionally, extracellular matrix refers to a collection of biopolymers which fill in the space within tissues or extracellular space. Extracellular matrix is present in all tissues, and in particular, is abundant in connective tissue. The extracellular matrix has been known to have the physical functions such as tissue support and binding, physical boundary, absorption of strength, and elasticity. Recent studies have revealed that extracellular matrix plays the physicochemical roles of controlling extracellularly such as cell proliferation, cell migration, intracellular metabolism, cell differentiation, and cell morphology.

The material for aggregating blood cells, which is included in the blood cell aggregating agent according to the present invention, also performs the functions of the extracellular matrix on the blood cells. However, the material for aggregating blood cells, instead of playing the physicochemical roles including cell proliferation, cell migration, and intracellular metabolism, plays the physical roles such as aggregation of blood cells, defense and absorption of physical factors being added thereto from the exterior of the blood cells, and elastic factors, and the material for aggregating blood cells performs the functions of preventing the damage and loss of the blood cells through them.

More specifically, the aggregation of the blood cells refers to the realization of each separate blood cell is physically formed into an aggregated form mediated by a material for aggregating blood cells (or a blood cell aggregating agent containing the same) or, and it may not refer to the aggregation resulted when the material for aggregating blood cells becomes a ligand and binds to the surface receptors of a cell membrane of the blood cells, or the aggregation of blood cells according to the chemical change of the material for aggregating blood cells. Accordingly, in an exemplary embodiment of the present invention, the material for aggregating blood cells may not include blood plasma components, and more preferably plasma proteins, e.g., fibrinogen, prothrombin, or thrombin or fibrin, which are in activated forms, and thus the aggregation of the blood cells by the material for aggregating blood cells may not be the aggregation by the conventional blood coagulation mechanism. When blood cells are aggregated by the blood coagulation mechanism there will be problems in that the red blood cells will be excessively included within the aggregating agent, and thus, even when they are prepared into paraffin blocks the amount of blood cells other than the red blood cells becomes too small thus decreasing the diagnostic usefulness, and additionally, the release of intracellular enzymes due to the erythrocytolysis can damage DNA and RNA of the blood cells thus deteriorating the diagnostic values of the prepared aggregating agent for the blood cells and the objects of the present invention cannot be achieved using the plasma proteins.

The material for aggregating blood cells included in the blood cell aggregating agent according to the present invention can exhibit the functions described above, and thus the material may be advantageous in preparing the blood cells into paraffin blocks. The conventional subjects for paraffin blocks are first prepared as cell blocks and then treated with paraffin, and the subjects for paraffin blocks are biotissues. In the conventional biotissues, cells with intercellular adhesion aggregated to form a block and each of the cells forming the block can be further aggregated with the cells on the outside including extracellular matrix and the cells themselves can be physically protected. However, each of the blood cells independently floats within the blood unlike the biotissues, has no intracellular adhesion, and also does not include the materials for performing the extracellular matrix on the exterior of the cell membrane. When the blood cells having these properties are prepared into cell blocks, the blood cells cannot be aggregated and thus it is difficult to prepare cell blocks themselves, and in addition, when the unaggregated cells go through with several steps for the preparation of paraffin blocks the targeted particular types of blood cells may be lost. Additionally, since the blood cells cannot be protected, the targeted particular types of blood cells may be damaged as they go through with several steps for the preparation of paraffin blocks, and, during the process of treating paraffin melted by heating at 60° C. or higher, the targeted particular types of blood cells may be lost. The material for aggregating blood cells included in the blood cell aggregating agent according to the present invention can perform the functions of extracellular matrix regarding the blood cells to resolve the above problems, and thus it can aggregate the blood cells and prevent the damage or loss of the blood cells during the process of preparing paraffin blocks.

According to an exemplary embodiment of the present invention, the material for aggregating blood cells may contain gelatin.

Specifically, gelatin can be used for a variety of uses such as foods or for industrial use. Gelatin simply swells in cold water but becomes sol in warm water. Gelatin is a heat-stable molecule, which, at a concentration of 2% to 3% or higher, becomes a gel when cooled, and thus it may be suitably used as the material for aggregating blood cells of the present invention. Additionally, gelatin has an excellent effect of preventing damage and loss of blood cells when it is used alone for aggregating blood cells, compared to other kinds of materials capable of performing the extracellular matrix, and is thus more advantageous in preparing paraffin blocks with excellent physical properties aimed at in the present invention. As the material for aggregating blood cells, gelatin may contain collagen. Preferably, the gelatin may be included in the state of a gelatin solution mixed with a solvent. The solvent may be a phosphate buffer solution, distilled water, saline, etc., and in an exemplary embodiment of the present invention, the solvent may be distilled water.

Additionally, gelatin to be included as the material for aggregating blood cells may be preferably contained in the blood cell aggregating agent for preparing paraffin blocks at a concentration of 5 mg/mL to 35 mg/mL, more preferably 5 mg/mL to 30 mg/mL, and most preferably 5 mg/mL to 20 mg/mL. When the gelatin concentration is below 5 mg/mL, the preparation of paraffin blocks from the blood cells will require a longer time thus causing damage to the blood cells, or the gelatin may be melted thus significantly deteriorating the sensitivity and specificity in the diagnosis of blood cells. Additionally, when the gelatin concentration exceeds 35 mg/mL, it will increase the hardness of the resulting paraffin blocks thus causing the paraffin sections may be bounced off or become fragile to induce the loss of the blood cells, thereby significantly deteriorating the sensitivity and specificity in diagnosing blood cells. Specifically, as can be confirmed in Table 5 below in which the recovery rate of the CTCs according to the change in gelatin concentration was compared, when the gelatin concentration was 10 mg/mL the recovery rate of the CTCs was significantly low to become 68%, whereas when the gelatin concentration was 50 mg/mL the recovery rate of the CTCs was only 6%.

Meanwhile, the material for aggregating blood cells may further include at least one material selected from the group consisting of pectin, chondroitin sulfate, fibronectin, starch, and laminin. By further containing the above material, the sensitivity and specificity for the blood cells can be improved when they are prepared into paraffin blocks. In particular, since the gelatin feature can change according to the temperature at varied concentrations, when gelatin is included as the material for aggregating blood cells, and the gelatin concentration is increased to obtain a solid phase or semi-solid phase at a particular temperature range, the intended feature may be obtained but the sensitivity and specificity for the blood cells may be significantly deteriorated. For example, according to an exemplary embodiment of the present invention, when gelatin is placed in a room at 28° C. at a concentration of 20 mg/mL for more than 10 minutes, gelatin will turn into a liquid phase (see Table 6 below). When the gelatin concentration is increased higher than 20 mg/mL to maintain gelatin in a semi-solid phase, the gelatin feature may be maintained in a solid or semi-solid phase, however, the sensitivity and specificity of the targeted paraffin blocks for the CTCs may not be achieved. Specifically, in Table 5 below, when the gelatin concentration was 30 mg/mL the recovery rate of the paraffin blocks of the CTCs was 80%, whereas when the gelatin concentration was 50 mg/mL the recovery rate of the paraffin blocks of the CTCs was significantly lowered to 6%, thus confirming that at a certain gelatin concentration or higher, the increase in gelatin concentration increases the recovery rate of the CTCs thereby significantly deteriorating the sensitivity and specificity of the paraffin blocks for the CTCs.

Accordingly, for the maintenance of the intended gelatin feature at a particular room temperature, in order to conserve the sensitivity and specificity of the paraffin blocks for the blood cells deteriorated according to the gelatin concentration, at least one material selected from the group consisting of pectin, chondroitin sulfate, fibronectin, starch, and laminin may be further added to the material for aggregating blood cells, and in this case, the intended feature at a particular temperature can be maintained, while being more advantageous in simultaneously exhibiting the sensitivity and specificity of the paraffin blocks for the blood cells.

Preferably, the material being further added in addition to gelation as the material for aggregating blood cells may be contained in a range of less than 5%. When the material being further added in addition to gelation as the material for aggregating blood cells is contained in excess of 5%, the hardness of the resulting paraffin blocks may be broken or become fragile during the thin-cutting process and cause the loss of the blood cells thereby deteriorating the sensitivity and specificity of the diagnosis for the blood cells.

Meanwhile, when only the material being further added as the material for aggregating the blood cells in addition to gelatin is added, without containing gelatin being added to the material for aggregating blood cells, the intended properties may not be obtained. Specifically, starch is easy to use but it can be readily separated, and once it is cooled after adjustment of the concentration, the initial viscosity or quality cannot be reproduced although it is heated again. Additionally, starch is not dissolved in cold water but has a physical property that it becomes gelatinized when placed in warm water, thus making it difficult to prepare paraffin blocks. Additionally, when the starch concentration is increased to a high concentration for improving the aggregation of blood cells, it will improve the aggregating force but it will excessively increase the hardness thus causing the paraffin blocks to become broken or fragile during the process of thin-cutting paraffin blocks, and in particular, it may cause the damage and loss of the blood cells, and thus the use of starch alone as the material for aggregating the blood cells may be restrictive.

Additionally, the pectin, being a polymer of carbohydrates, can be used in foods as a coagulant, a thickener, a stabilizer, an anticaking agent, an emulsifying agent, etc., and the thickening property and gelling property vary according to the balance between acid and ester, and in the case of the acid content not exceeding 50% or non-esterified pectin, there is a strong tendency of forming a gel with calcium ions and thus the use of pectin alone as the material for aggregating the blood cells may be restrictive.

Additionally, since fibronectin and laminin are not heat-stable and thus their use as the material for aggregating the blood cells may be restrictive.

When gelatin is included as the material for aggregating blood cells, it will be difficult to confirm the presence of jelly within a container by the naked eye because gelatin is colorless and transparent. Therefore, the material for aggregating the blood cells of the present invention may further contain a color fixing agent for color development.

The coloring agent may include Bromophenol Blue, Carbon Black, N,N-dimethylaminoethanol, Copper Phthalocyanine, Pennsperse Orange, etc., and preferably, the color fixing agent for fixing the colors of the material for aggregating blood cells according to an exemplary embodiment of the present invention may be a loading buffer containing Bromophenol Blue (Takara Bio Inc). The coloring agent may be contained in the blood cell aggregating agent for preparing paraffin blocks in an amount from 5 volume parts to 10 volume parts relative to 100 volume parts of the material for aggregating blood cells. When the color fixing agent is contained more than 10 volume parts relative to 100 volume parts of the material for aggregating blood cells, the aggregating force of a specimen. When the color fixing agent is contained more than 10 volume parts relative to 100 volume parts of the material for aggregating blood cells, there is a problem in that the aggregating force of the specimen is weakened or the aggregation of the specimen is delayed, whereas when the color fixing agent is contained less than 5 volume parts, the effect of color development by formalin fixation disappears thus making the embedding of the specimen becomes difficult.

Meanwhile, according to an exemplary embodiment of the present invention, a diagnostic kit for CTCs including a blood cell aggregating agent for preparing paraffin block according to the present invention may be embodied.

There is no limitation regarding the cancer types that the diagnostic kit for CTCs can be used for the diagnosis, but it is known that there is only one CTC present per one million blood cells in the blood of cancer patients. The diagnostic kit of the present invention can include cancer types to be diagnosed by confirming the CTCs, which are rare tumor cells present in the blood and circulate throughout the body. Accordingly, the diagnostic kit of the present invention may be used for the diagnosis of metastatic breast cancer, colorectal cancer, liver cancer, or prostate cancer, in which the presence of the CTCs, although being present in an extremely small amount in the blood, has been identified as an important prognosis factor associated with survival rate.

The diagnostic kit for CTCs of the present invention may further contain a color fixing agent for color development of the material for aggregating blood cells in an amount of from 5 volume parts to 10 volume parts relative to 100 volume parts of the material for aggregating blood cells contained in the blood cell aggregating agent. For example, when the amount of the blood cells is 40 µL, the aggregation of the blood cells and a gelatin solution in the form of a jelly can be confirmed by adding 40 µL of a gelatin solution and 2 µL of a color fixing agent to the blood cells. The criticality of the amount of the color fixing agent is the same as described above and thus the explanation thereon is omitted.

Meanwhile, the method of preparing a paraffin block according to the present invention in light of the blood cell aggregating agent for preparing the paraffin block includes (1) removing red blood cells from the blood of a subject and extracting blood cells therefrom; (2) mixing the blood cells with the blood cell aggregating agent according to the present invention to prepare blood cell aggregates; (3) curing the blood cell aggregates; and (4) treating the paraffin block forming material on the cured product according to step (3). By the method, the blood cells (cell pellet) obtained from a small amount of blood can be prepared into paraffin blocks without damage, loss, etc., of the blood cells, and the thus-prepared paraffin blocks can be used to perform experiments for the analysis of particular types of blood cells with only a single blood sample collection of 5 mL to 6 mL from a subject up to 50 times to 60 times. Therefore, the method has a wide range of application in both pathological and clinical aspects, and may be used for useful test methods. Specifically, simplification, cost-effectiveness, and high reliability can be achieved in cancer diagnosis through the development of comprehensive cancer diagnostic tools and methods by securing novel innovative technologies in selection, recovery, and biological analysis of CTCs.

First, step (1) includes removing red blood cells from the blood sample of a subject followed by extracting blood cells therefrom.

The red blood cells account for the highest percentage in terms of number among the blood cells, and when the blood cells including red blood cells are prepared into paraffin blocks, the probability that the targeted particular type of blood cells can be included in the blood cells, which are to be included per unit area of the thus-prepared paraffin block sections, may be very low. Additionally, when red blood cells are damaged or destroyed during the process of paraffin block preparation, various kinds of enzymes that may affect the cell membranes, DNA, RNA, cytoplasm, etc., of particular types of blood cells may be released, thus making the diagnosis of the targeted particular blood cells very disadvantageous or impossible. Accordingly, in preparing paraffin blocks for the diagnosis of CTCs, it is essential to extract only the blood cells free of red blood cells from the blood sample collected from a subject.

Meanwhile, according to the conventional method for the diagnosis of CTCs, not only red blood cells but also white blood cells were removed from the blood sample collected from a subject by subjecting the blood cells with various chemical and physical treatments thereby extracting the final CTCs. However, the conventional method had problems in that the method could induce the loss of the CTCs via several times of centrifugation while undergoing various steps up to the final extraction of the CTCs, and also could deteriorate the recovery rate of the CTCs. In contrast, the method of the present invention prepares cell blocks employing the blood cells only free of red blood cells from the blood sample collected from a subject, and thus the method is a very efficient method which can considerably simplify the preparation process, reduce the preparation time, has low rate of cell loss for not necessitating physical or chemical treatment on the CTCs, and also has very high cell preservation rate.

The method of removing red blood cells to be used in step (1) according to the present invention may include the conventional centrifugation, inverted centrifugation, filtration, dextran method, cytolysis method, etc., although not limited thereto, and more preferably by Ficoll treatment method. Specifically, as can be confirmed in Experimental Example 3 below, in the paraffin blocks prepared using the blood cells by spiking 4000 cells of colorectal cancer cell line SW620 into normal blood followed by respectively treating with Ficoll and cell lysis buffer to remove red blood cells, the recovery rate of the CTCs (calculated by counting the total number of the CTCs included in the paraffin blocks after cytokeratin (CK) staining) was subjected to comparative analysis. As a result, it was confirmed that the recovery rate was a 1.7-fold higher on average when the paraffin blocks were prepared by removing red blood cells via Ficoll treatment method, compared to that via cell lysis buffer method.

Additionally, according to an exemplary embodiment of the present invention, the tube used in step (1), into which the blood cells are extracted, may be coated with a blood cell aggregating agent. The coating refers to coat the bottom surface of the tube, into which the blood cells are extracted, with the blood cell aggregating agent, which has the same composition as that of the blood cell aggregating agent to be mixed in the blood cells in step (2). In particular, the coating is preferably coated to have a constant thickness to avoid becoming too thick or too thin for easy recovery of the blood cells, and preferably a thickness of the coating 1 mm to 2 mm.

The reason of coating the tube, into which the blood cells are extracted, in advance with a blood cell aggregating agent is to prevent the damage, loss, and/or vanishing of blood cells (cell pellet) when the blood cell aggregates being obtained via step (2) below is separated from the tube, and the recovery of the blood cell aggregates can be facilitated by coating the tube to be used in step (1) with the blood cell aggregating agent in advance.

Then, step (2) of the present invention includes preparing the blood cell aggregates by mixing the blood cells extracted in step (1) with the blood cell aggregating agent for preparing paraffin blocks according to the present invention. The blood cell aggregating agent for preparing paraffin blocks according to the present invention performs the functions of extracellular matrix on the blood cells free of red blood cells, thereby capable of maintaining the CTCs from being lost and the cytoplasm from being damaged, and by doing so, the antigenicity of the CTCs can be maintained.

The explanations on the blood cell aggregating agent for preparing paraffin blocks according to the present invention are the same as described above and are thus omitted.

According to an exemplary embodiment of the present invention, the blood cell aggregating agent for preparing paraffin blocks is preferably contained in an amount of from 80 volume parts to 10 volume parts relative to 100 volume parts of the blood cells (cell pellet), and as such, the blood cell aggregating agent will be more advantageous for the achievement of the physical properties of the intended paraffin blocks.

Meanwhile, when gelatin is used as the material for aggregating blood cells to be included in the blood cell aggregating agent for preparing paraffin blocks according to the present invention, the feature of the blood cell aggregates may vary at a particular temperature according to the gelatin concentration contained in the blood cell aggregating agent, and thus the gelatin concentration may be adjusted in consideration of the temperature to perform step (2), and preferably, any of the conditions from (a) to (c) may be satisfied.

(a) The gelatin concentration in the nucleated cell aggregating agent in the blood cells is from 5 mg/mL to 15 mg/mL, when step (2) is performed at a temperature between 5° C. or higher and lower than 15° C.

(b) The gelatin concentration in the nucleated cell aggregating agent in the blood cells is from 15 mg/mL to 25 mg/mL, when step (2) is performed at a temperature between 15° C. or higher and lower than 25° C.

(c) The gelatin concentration in the nucleated cell aggregating agent in the blood cells is from 25 mg/mL to 35 mg/mL, when step (2) is performed at a temperature between higher than 25° C. and lower than 35° C.

When the gelatin is contained as the material for aggregating blood cells, if any of the conditions from (a) to (c) is not satisfied, gelatin is melted in the blood cell aggregates prepared in step (2) thus the blood cell aggregates be separated from the tube, and thus it becomes difficult to prepare the intended blood cell aggregates, and also the process of step (3) below may be difficult to proceed with.

Accordingly, the concentration that the coagulated gelatin begins to melt varies according to the temperature for performing step (2), and thus it is preferable to change the concentration of the solution in consideration of the temperature for performing step (2).

Additionally, a color fixing agent for color development of the blood cell aggregating agent may be further included in step (2), and the color fixing agent may be further contained in an amount of from 5 volume parts to 10 volume parts relative to 100 volume parts of the material for aggregating blood cells included in the blood cell aggregating agent. The explanation on the color fixing agent is the same as described above and is thus omitted.

Meanwhile, it is preferable that the process of from extracting blood cells after separating red blood cells from the blood sample of a subject in step (1) to preparing the blood cell aggregates by administering the blood cell aggregating agent for preparing paraffin blocks of gelation, etc., in step (2) be finished within two hours from the collection of the blood sample from the subject. This is because the CTCs included in the peripheral blood of the collected blood can easily undergo apoptosis, compared to the white blood cells.

Specifically, as shown in FIG. 5, as a result of the cell spiking test on normal blood using a breast cancer cell line, the cytological features of the paraffin blocks prepared one hour after the blood collection and those prepared two hours after the blood collection revealed that the cytoplasm of cancer cells is degraded two hours after the collection of blood sample and the antigenicity is also deteriorated.

Then, step (3) of the present invention of curing the blood cell aggregates prepared in step (2) is performed.

The curing of the blood cell aggregates, which was prepared in step (2), can facilitate the separation of the blood cell aggregates from the tube, reduce the no-treatment time for general biopsy tissues (generally 12 hours or more) used for the preparation of paraffin blocks to 6 hours or less, facilitate the treatment of the paraffin block forming material through step (4) described below, and be more advantageous to prepare the paraffin blocks with intended physical properties. Preferably, the curing in step (3) may be performed by placing the blood cell aggregates prepared in step (2) at a temperature of from 2° C. to 5° C. for from 15 minutes to 30 minutes to cure the blood cell aggregates into a form of jelly. The cured blood cell aggregates may be fixed by placing in formalin, methanol, etc., for the preservation of the cells.

Then, step (4) of the present invention of treating the cured product prepared in step (3) with a paraffin block forming material is performed.

The paraffin block forming material may include alcohol, xylene, and paraffin, and paraffin blocks may be prepared via autopenetration process by sequentially treating the cured product prepared in step (3) with the paraffin block forming material of alcohol, xylene, and paraffin in this order.

Specifically, the autopenetration process may be performed by wrapping the cured product with paper and then treating with alcohol, xylene, and paraffin in this order. The reason of performing the autopenetration process is as follows. First, for the thin-cutting of the specimen for microscopic observation, water may be removed from the specimen fixed using a fixative to enable the paraffin penetration (step of alcohol treatment). Then, although the water contained in the specimen may be removed by alcohol treatment, alcohol and paraffin do not mix with each other and thus alcohol may be removed using xylene (step of xylene treatment). Finally, for the microscopic observation of the specimen, the specimen is required to be cut thinly, and thus the paraffin penetration process may be performed for the specimen in order to perform the thin-cutting (step of paraffin treatment).

In particular, the step of alcohol treatment may be performed in several divided steps according to the amount or size of the specimen, for example, the alcohol treatment may be performed first with a low concentration alcohol (possibly a multiple treatment) followed by a high concentration alcohol (possibly a multiple treatment). The multiple treatment may also be applied to the step of xylene treatment and the step of paraffin treatment in the same manner.

Additionally, the present invention provides a method for microscopic observation of paraffin blocks prepared by the method described above, and this method includes a thin-cutting of paraffin blocks prepared by the method described above into an appropriate size to be prepared into sections, staining the thinly cut paraffin blocks and observing the same.

The thin-cutting process may be performed using a conventional thin-cutting machine such as a microtome, and a staining process may be performed using a staining reagent commonly used in the art.

The paraffin blocks prepared according to the present invention by performing the autopenetration process can be observed via sectioning by thinly cutting them to a thickness of from 3 µm to 10 µm followed by immunohistochemical staining.

Paraffin blocks are generally cut into a thickness of from 4 µm to 5 µm. However, in the present invention, the number of CTCs may be counted by thinly cutting the paraffin blocks to a thickness of from 3 µm to 10 µm preferably from 5 µm to 8 µm, and more preferably from 7 µm to 8 µm, in consideration of the size of the CTCs.

When the paraffin blocks according to the present invention are cut to a thickness of 7 µm to 8 µm, with a collection of 6 mL of blood, 30 tests can be performed, and when the paraffin blocks are cut to a thickness of 3 µm to 4 µm, 60 tests can be performed. Accordingly, only a single collection of a small amount of a blood sample enables a few tens of tests thus allowing the application of other markers in each test. Additionally, by performing multiple tests at time intervals, the method can be a useful test method with a wide range of application from both the clinical and pathological aspects.

The immunohistochemical staining may be performed using the staining reagents commonly used in the art, without limitation, and according to an exemplary embodiment of the present invention, the staining may be H & E staining or cytokeratin (CK) immunohistochemical staining.

Histological, immunohistochemical, and molecular biological tests on CTCs may be performed by microscopic observations on specimens using paraffin blocks prepared by the methods described above.

Specifically, as can be confirmed in Experimental Example 8 below, the morphological confirmation and counting the number of CTCs can distinguish the CTCs from contaminated epithelial cells, and thereby provide an accurate diagnosis without determination of false-positives.

Additionally, as can be confirmed in Experimental Example 3 and Experimental Example 4 below, it is possible to perform an immunohistochemical test by selecting the intended surface markers, without limitation. Furthermore, the CTCs can be detected with higher sensitivity by combining the tissue-specific markers shown in Table 1 below, which are already used in the pathological diagnosis of metastatic cancer with uncertain primary sites.

TABLE 1

<Tissue-specific diagnostic markers currently used in pathological diagnosis per primary site>

| Primary Site | Diagnostic Marker |
|---|---|
| Breast | GCDFP-15, ER |
| Colon | CK 20, CDX2 |
| Lung | TTF1 |
| Ovary | ER, mesothelin |
| Prostate | PSA |
| Stomach or Pancreas | CK7, CK20, MUC5AC |

Additionally, it is possible to perform molecular biological tests such as fluorescence in situ hybridization (FISH) and mutation analysis.

Therefore, even with the development in technologies in the fields of laboratory medicine and radiology for cancer diagnosis, these methods are still restrictive in providing accurate diagnosis. The most accurate cancer diagnosis is a pathological diagnosis by histological examination, however, the method of the present invention can be an effective method of diagnosis for the group of patients with terminal cancer who cannot receive surgical treatment or get an access to histological examination.

MODE FOR CARRYING OUT THE INVENTION

Hereinafter, the present invention will be described in more detail with reference to the following Examples. However, these Examples are for illustrative purposes only, and the invention is not intended to be limited by these Examples.

Example 1

1-1. Blood Collection

The peripheral blood of a normal person in an amount of 6 mL was collected into a tube, and the number of white blood cells in the blood sample was counted as $4 \times 10^7$. Four thousand cancer cells of the colorectal cancer cell line SW620 were spiked to comply with the ratio (white blood cells:cancer cells=10,000:1) and stored at room temperature.

1-2. Separation of Red Blood Cells

Three 15 mL tubes were prepared for 6 mL of each collected peripheral blood, and 5 mL of Ficoll was aliquoted into each 15 mL tube, respectively. Then, all the blood collected in EDTA tubed was transferred into a 50 mL tube, added with 2 volumes of phosphate buffer solution (PBS) and mixed.

The PBS-containing Ficoll in the amount of 7 mL was aliquoted to the Ficoll contained in the 15 mL tubes, respectively, centrifuged at 2000 rpm for 20 minutes. After confirming the presence of the three layers of serum, Ficoll, and a white buffy coat layer between serum and Ficoll, only the white cell layer concentrated in the buffy coat layer was carefully recovered. Then, the recovered cells were transferred into a fresh 50 mL container, added with PBS to a final volume of 50 mL, and centrifuged at 1500 rpm for 10 minutes. The resulting supernatant was recovered from the tube upon completion of the centrifugation, and the cell pellet was added with 1 mL of PBS, centrifuged at 13000 rpm for 3 minutes, and blood cells free of red blood cells were obtained.

1-3. Preparation of a Blood Cell Aggregating Agent for Preparing Paraffin Blocks First, the gelatin solution was melted in warm water at a temperature from 90° C. to 100° C. with the material for aggregating blood cells to prepare a gelatin solution at a concentration of 10 mg/mL. The gelatin solution was placed at room temperature to cool it down to 22° C. for use.

Before mixing the blood cells free of red blood cells with a blood cell aggregating agent, an empty tube was injected with a gelatin solution to a thickness of 1 mm after the tube was coated in advance with the gelatin solution at the same concentration, and the blood cells were added into the tube, which was coated in advance, and the gelatin solution was mixed with the blood cells contained in the tube at a 1:1 volume ratio. Additionally, for the confirmation of aggregation of the transparent gelatin solution, a loading buffer (Takara Bio Inc) containing 0.05% Bromophenol Blue as a color fixing agent was added at a 1:0.05 volume ratio relative to the gelatin solution.

After confirming that the mixture of the blood cells/a gelatin solution/a color fixing agent was cured by being hardened in the form of a jelly by storing the mixture of the blood cells/the gelatin solution/the color fixing agent at 4° C. for 20 minutes, the cured product was separated from the tube, transferred into a 15 mL tube and added with 10 mL of neutral formalin, and stored at room temperature for 18 hours.

1-4. Preparation of Paraffin Blocks

Paraffin blocks were prepared using the cured product of the blood cell aggregates prepared in Example (1-3).

The conventional process for treating tissues requires at least 12 hours. The method of preparing paraffin blocks in the present invention, although based on the conventional process, can reduce the tissue treatment process to 6 hours thereby reducing the preparation time and simplifying the preparation process.

Paraffin blocks were prepared according to the tissue treatment process shown in Table 2 below.

TABLE 2

|  | Process of Performance | Time for Performance (Min) |
| --- | --- | --- |
| 1 | Formalin | 60 |
| 2 | Distilled Water | 5 |
| 3 | 99.9% Alcohol (1) | 15 |
| 4 | 99.9% Alcohol (2) | 15 |
| 5 | 99.9% Alcohol (3) | 30 |
| 6 | 99.9% Alcohol (4) | 30 |
| 7 | 99.9% Alcohol (5) | 30 |
| 8 | 99.9% Alcohol (6) | 30 |
| 9 | Xylene (1) | 30 |
| 10 | Xylene (2) | 60 |
| 11 | Paraffin (1) | 30 |
| 12 | Paraffin (2) | 60 |

Upon completion of the process in Table 2, the resultants were prepared into blocks by embedding them into paraffin and stored thereafter.

In the process shown in Table 2, ethanol was used as the alcohol (Fisher Scientific), and xylene (DUKSAN) and paraffin (Histosec Pastillen, MERCK) were used.

Example 2

Paraffin blocks were prepared in the same manner as in Example 1 except that a lysis buffer was used instead of Ficoll for the separation of red blood cells in (1-2) of Example 1.

Examples 3 to 7

Paraffin blocks were prepared in the same manner as in Example 1 except that the gelatin concentration was varied into 3 mg/mL, 20 mg/mL, 30 mg/mL, 40 mg/mL, and 50 mg/mL, respectively, instead of 10 mg/mL in (1-3) of Example 1.

Examples 8 and 9

Paraffin blocks were prepared in the same manner as in Example 1 except that cancer cells were spiked so that the ratio between the number of the cancer cells being spiked in (1-1) of Example 1 and the number of white blood cells in the blood cells was changed to 1:10$^5$ and 1:10$^6$, respectively, instead of 1:10$^4$.

Example 10

Paraffin blocks were prepared in the same manner as in Example 1 except that a breast cancer cell line, SKBR3, was used as the cancer cell type being spiked in (1-1) of Example 1 instead of the colorectal cancer cell line SW620, and also Example 1-2 was performed after placing the blood for one hour thereat after performing Example 1-1, instead of performing Example 1-2 immediately after performing Example 1-1.

Example 11

Paraffin blocks were prepared in the same manner as in Example 10 except that Example 1-2 was performed after placing the blood for two hours thereat after performing Example 1-1, instead of performing Example 1-2 after placing the blood for one hour thereat after performing Example 1-1.

Examples 12 to 21

Paraffin blocks were prepared in the same manner as in Example 1 except that the ratio between the number of the cancer cells being spiked in (1-1) of Example 1 and the number of white blood cells in the blood cells was changed to 1:10$^5$ instead of 1:10$^4$, and the material for aggregating blood cells in (1-3) of Example 1 was changed as shown in Table 7 below.

Comparative Example 1

Four thousand cancer cells were spiked into 6 mL of normal blood, treated with Ficoll to remove red blood cells, and the resulting extracted blood cells were fixed by adding formalin thereto for 18 hours. The fixed specimen was centrifuged, and the supernatant was removed. The resulting precipitate of the specimen was recovered and added with polyvinyl alcohol and distilled water. The mixture was added with acetone and cyanoacrylate and subjected to a further centrifugation. The resulting supernatant was removed and the precipitate of the specimen was recovered. An autopenetration was performed for the precipitate after preparation of paraffin blocks, the entire paraffin blocks were prepared into continuous paraffin block sections with a thickness of 8 μm and each section was subjected to CK staining to count the number of CTCs included in the each block.

Experimental Example 1

Detection of CTCs Via Immunohistochemical Staining

The paraffin block sections prepared by thin-cutting of the paraffin blocks to a thickness of 8 μm prepared in Example 1 were subjected to cytokeratin (CK) staining and the pictures observed are shown in FIG. 2.

Specifically, as shown in FIG. 2, when the paraffin block sections prepared by thin-cutting of the paraffin blocks were subjected to immunohistochemical staining, it was confirmed that the brown cells observed therein were CTCs.

Experimental Example 2

Analysis of Recovery Rate of CTCs Derived from a Cancer Cell Line

For the measurement of sensitivity in the analysis of CTCs by the paraffin blocks for the detection of CTCs prepared in Example 1 and Comparative Example 1, the recovery rate of the CTCs included in the paraffin blocks were subjected to a comparative analysis.

Considering the size of CTCs, the entire paraffin blocks were prepared into continuous paraffin block sections with a thickness of 8 μm and each section was subjected to CK staining to count the number of CTCs included in the entire blocks. The average values for the paraffin blocks prepared by performing Example 1 and Comparative Example 1 three times, respectively, are shown in Table 3 below.

TABLE 3

|  | No. of Sections | No. of Cancer Cells per Section | Recovery Rate of Total Cancer Cells |
| --- | --- | --- | --- |
| Comparative Example 1 | 56 | 22 ± 1.3 | 1017 (25%) |
| Example 1 | 30 | 122 ± 4.8 | 3732 (93%) |

Specifically, as shown in Table 3 above, the average recovery rate of the CTCs by the paraffin blocks prepared in Example 1 was 93%, which was 3.7 times higher than the recovery rate of the CTCs by the paraffin blocks prepared in Comparative Example 1.

Additionally, the number of thinly-cut sections from the paraffin blocks prepared according to Example 1 was 30, which was lower than that from the paraffin blocks prepared by Comparative Example 1. However, the number of the CTCs included in each section from the paraffin blocks prepared according to Example 1 was significantly higher than that from the paraffin blocks prepared by Comparative Example 1.

Referring to the results shown in Table 3 above, the result on Comparative Example 1 is due to the loss and/or damage of CTCs by the two additional centrifugation after the separation of red blood cells, and accordingly, it was confirmed that in Example 1, the damage or loss of CTCs by centrifugation was significantly reduced.

Additionally, in order to melt paraffin during the process of preparing sections using paraffin blocks, paraffin should be heated to 60° C. In this regard, it was confirmed that there was a loss of the blood cells during the process in Comparative Example 1, whereas, in Example 1, a blood cell aggregating agent is used for the paraffin blocks thus reducing the loss of the blood cells during the heat treatment.

Additionally, it was confirmed that the paraffin blocks prepared in Example 1 are thinly cut to a thickness of 8 μm, they can be used for 30 times of tests, and when paraffin blocks are cut to a thickness of 4 μm, they can be used for 60 times of tests, and different markers may be applied in each test.

Experimental Example 3

Analysis of Recovery Rate of Cancer Cells According to the Method of Removing Red Blood Cells The recovery rates of CTCs by the paraffin blocks prepared in Examples 1 and 2 (the recovery rates were calculated by counting the total number of CTCs included in the paraffin blocks after CK immunohistochemical staining) were counted and the results are shown in Table 4 below.

TABLE 4

| | Method of Removing Red Blood Cells | No. of Recovered Cancer Cells |
|---|---|---|
| Example 1 | Ficoll | 2252 ± 08.3 |
| Example 2 | Lysis Buffer | 1291 ± 98.4 |

Specifically, as shown in Table 3 above, upon comparison of the recovery rate of CTCs, it was confirmed that Ficoll treatment method has a 1.7-fold higher rate on average compared to the cytolysis method. Accordingly, it was confirmed that Ficoll treatment is more excellent in removing red blood cells from the blood for the preparation of paraffin blocks with excellent physical properties.

Experimental Example 4

Analysis of Recovery Rate of CTCs According to the Concentration of Gelatin Solution The recovery rates of CTCs by the paraffin blocks prepared in Examples 1 and 3 to 7 (the recovery rates were calculated by counting the total number of CTCs included in the paraffin blocks after CK immunohistochemical staining at room temperature (20° C.)) were counted and the results are shown in Table 5 below.

TABLE 5

| | Conc. of Gelatin Solution (mg/mL) | Recovery Rate of CTCs |
|---|---|---|
| Example 3 | 3 | 68% |
| Example 1 | 10 | 93% |
| Example 4 | 20 | 86% |
| Example 5 | 30 | 80% |
| Example 6 | 40 | 23% |
| Example 7 | 50 | 6% |

As a result of comparison of recovery rate of CTCs according to the change in the concentration of the gelatin solution, as shown in Table 5 above, the recovery rate of CTCs was high at room temperature in Examples 1, 4, and 5, whereas the recovery rate of CTCs in Examples 3, 6, and 7 was significantly reduced. In particular, in Example 5, when the concentration of the gelatin solution was 30 mg/mL, the recovery rate of CTCs was 80%, whereas, in Example 6, when the concentration of the gelatin solution was 40 mg/mL, the recovery rate of CTCs was 23%, thus showing a decrease by 57% (the decrease of the recovery rate of CTCs was tantamount to 71.2%).

Experimental Example 5

Analysis of Lysis at Various Room Temperatures According to the Concentration of Gelatin Solution Regarding the gelatin solution (50 μL) used in Examples 1, 4, and 5, the presence of dissolution was evaluated at varied room temperature conditions of 5° C., 17° C., and 28° C., respectively, according to the no-treatment time. The results were indicated as "x" in the case of undissolution and "o" in the case of dissolution, as shown in Table 6 below.

TABLE 6

| | 10 mg/mL | | | 20 mg/mL | | | 30 mg/mL | | |
|---|---|---|---|---|---|---|---|---|---|
| Time for No-Treatment | 5° C. | 17° C. | 28° C. | 5° C. | 17° C. | 28° C. | 5° C. | 17° C. | 28° C. |
| 5 Min | x | x | o | x | x | x | x | x | x |
| 10 Min | x | o | o | x | x | o | x | x | x |
| 20 Min | x | o | o | x | x | o | x | x | x |
| 30 Min | x | o | o | x | x | o | x | x | x |
| 60 Min | x | o | o | x | o | o | x | x | o |

Specifically, as shown in Table 6 above, it was confirmed that the presence of dissolution varied according to the concentration of the gelatin solution. In fact, there were also cases that gelatin was not melted when the no-treatment time was short but gelatin became melted as the no-treatment time became longer.

Accordingly, it was confirmed that the concentration of the gelatin solution should be varied according to room temperature and seasons. During the winter season, in which the room temperature is below 15° C., a blood cell aggregates in the form of a jelly may be prepared even when the concentration of the gelatin concentration is lower than 10 mg/mL. In contrast, during the summer season, in which the room temperature is below 25° C., gelatin becomes melted when the gelatin concentration is lower than 10 mg/mL, and thus for the preparation of the blood cell aggregates in the form of a jelly, it is necessary that the gelatin concentration should be higher than 20 mg/mL.

Meanwhile, as can be confirmed in Experimental Example 4 described above, the recovery rate of CTCs by paraffin blocks significantly varied according to the gelatin concentration, and when the recovery rate of CTCs was higher when the concentration of gelatin solution was 30 mg/mL than when the concentration of gelatin solution was 10 mg/mL. Accordingly, it was confirmed that, at the room temperature of from 5° C. to 15° C., the best blood cell aggregates and simultaneously the paraffin blocks with significantly excellent physical properties could be prepared, when the concentration of gelatin solution for the preparation of paraffin blocks is in the range of 5 mg/mL to 15 mg/mL.

Additionally, it was confirmed that, at the room temperature of from 15° C. to 25° C., the best blood cell aggregates and simultaneously the paraffin blocks with significantly excellent physical properties could be prepared, when the concentration of gelatin solution for the preparation of paraffin blocks is in the range of 20 mg/mL to 30 mg/mL.

Additionally, it was confirmed that, at the room temperature of from 25° C. to 35° C., the best blood cell aggregates and simultaneously the paraffin blocks with significantly excellent physical properties could be prepared, when the concentration of gelatin solution for the preparation of paraffin blocks is 30 mg/mL, and as the room temperature increased there was a problem that the coagulated gelatin solution was easily melted. However, the use of an extremely high concentration of gelatin solution to solve the problem will lower the recovery rate of the CTCs, as can be seen in Table 5 above. Accordingly, based on the results shown in Tables 5 and 6, it was confirmed that, at the room temperature of from 25° C. to 35° C., the best blood cell aggregates and simultaneously the paraffin blocks with significantly excellent physical properties could be prepared, when the concentration of gelatin solution is in the range of 25 mg/mL to 35 mg/mL.

Experimental Example 6

Analysis of Recovery Rate of CTCs According to the Material for Aggregating Blood Cells The recovery rates of CTCs by the paraffin blocks prepared in Example 12 (the recovery rates were calculated by counting the total number of CTCs included in the paraffin blocks after CK immunohistochemical staining at room temperature (20° C.)) were counted and the results are shown in Table 7 below.

Experimental Example 7

Analysis of Sensitivity of CTCs Via Paraffin Blocks

The paraffin blocks prepared in Example 1, Example 8, and Example 9 were subjected to CK immunohistochemical staining, and the pictures observed under a microscope are shown in FIG. 3.

Specifically, as shown in FIG. 3, it was confirmed that CTCs can be detected when the ratio between the colorectal cancer cell line SW620 and white blood cells is $1:10^6$ (Example 9). Based on this, it was confirmed that the method of preparing paraffin blocks for the detection of CTCs according to the present invention provides excellent sensitivity and specificity in the detection of the CTCs.

Experimental Example 8

Morphological Analysis of CTCs Via Paraffin Blocks

In the analysis of the CTCs regarding the paraffin blocks for the detection of CTCs according to the present invention, the detection of false-positives due to the contamination was confirmed via morphological confirmation.

TABLE 7

|  | Material for Aggregating Blood Cells | | | | No. of Spiked Cells | No. of Recovered Cells | Recovery Rate of CTCs |
| --- | --- | --- | --- | --- | --- | --- | --- |
|  | Gelatin (mg/mL) | Starch[1] (%)[4] | CS[2] (%) | Laminin[3] (%) |  |  |  |
| Example 12 | 20 | — | — | — | 400 | 344 | 86% |
| Example 13 | 20 | 1 | — | — | 400 | 203 | 50% |
| Example 14 | 20 | — | — | 0.001 | 400 | 154 | 39% |
| Example 15 | 30 | — | — | — | 400 | 320 | 80% |
| Example 16 | 30 | — | 0.25 | — | 400 | 220 | 55% |
| Example 17 | 30 | — | 0.5 | — | 400 | 321 | 80% |
| Example 18 | 30 | 1 | — | — | 400 | 203 | 51% |
| Example 19 | 30 | 2 | — | — | 400 | 345 | 86% |
| Example 20 | 30 | 5 | — | — | 400 | 308 | 77% |
| Example 21 | 30 | 1 | 0.125 | — | 400 | 352 | 88% |

[1]Starch (Sigma-Aldrich),
[2]CS: Chondroitin sulfate (Sigma-Aldrich),
[3]Laminin (Sigma-Aldrich),
[4](%): The contents of starch, CS, and laminin are concentration % based on gelatin, e.g., the starch content in Example 13 is 0.2 mg/mL.

Specifically, as can be confirmed in Table 7, Example 12 and Example 17, in which the gelatin solution was included alone as the material for aggregating blood cells, generally showed excellent recovery rate of CTCs compared to the cases when other materials for aggregating blood cells were included in addition to gelatin. However, the recovery rate of CTCs may be further improved according to the content of other kinds of materials for aggregating blood cells, and these can be confirmed in Examples 17, 19, and 21.

Cancer cells can be cytopathologically distinguishable from normal cells regardless of stainability. That is, in the conventional diagnostic method of CTCs by surface markers, normal epithelial cells with contamination could be diagnosed as false-positives because the presence of CTCs was determined according to the positive or negative result to the surface markers.

As a result of the CK immunohistochemical staining on the paraffin blocks prepared in Example 1, as shown in FIG.

4, it was confirmed that there could be a contamination of keratinocytes during the collection of blood samples or CK positive squamous cells detached from skin during the treatment of red blood cells or the process of preparing paraffin blocks, etc.

Accordingly, since the paraffin blocks for the detection of CTCs prepared according to the present invention enable the pathological examination, the presence of false positives can be confirmed by distinguishing the CTCs from the contaminated epithelial cells via morphological confirmation, and thus a more accurate diagnosis can be provided.

Experimental Example 9

Analysis of the Presence of Loss of Antigenicity of CTCs According to the No-Treatment Time of Blood Sample after Collection The paraffin blocks prepared in Example 1, Example 10, and Example 11 were subjected to CK immunohistochemical staining, and the pictures observed under a microscope are shown in FIG. 5.

Specifically, as can be confirmed in FIG. 5, as a result of comparison of the cytological features according to the no-treatment time until the process of removing red blood cells, it was observed that the cytoplasm of the CTCs was degraded and the antigenicity of the CTCs were deteriorated two hours after the blood collection.

Experimental Example 10

Various Application of Paraffin Blocks for Detection of CTCs

The applicability of various tests using the paraffin blocks for the detection of the CTCs prepared in Example 1 of the present invention was confirmed.

The CTCs derived from various cell lines were spiked to the normal blood at a ratio (white blood cells:cancer cells=10,000:1), and then the immunohistochemical staining and genetic tests were performed on various cancer diagnosis-specific markers. The results are shown in FIGS. 6 to 8.

Specifically, as shown in FIG. 6, a general H & E staining, c-erbB2 immunohistochemical staining, and fluorescence in situ hybridization (FISH) for Her2/neu gene were performed on the CTCs derived from a breast cancer cell line (SKBR3), and as a result, the gene expression was observed.

Additionally, as shown in FIG. 7, as a result of performing the immunohistochemical staining on the CTCs derived from a liver cancer cell line (HepG2), it was confirmed that the result was negative to EpCAM but positive to Glypican-3 and alpha-fetoprotein (AFP), which are liver cancer-specific markers.

Additionally, as shown in FIG. 8, as a result of performing the immunohistochemical staining on the CTCs derived from a colorectal cancer cell line (SW620), EpCAM expression was confirmed in the cytoplasmic membrane, and the nuclear expression of CDX2 and the expression of p53 protein, which are markers for the diagnosis of colorectal cancer, were also confirmed.

Experimental Example 10

Analysis of Cytological Characteristics of CTCs in Patients with Cancer Metastasis As an applicable example of a real patient, who received a sigmodiectomy in 2008 due to sigmoid colon cancer at stage 4, and had a recurrence in the liver in 2010, a blood sample was collected from the patient and the CTCs were confirmed using paraffin blocks prepared according to the method of the present invention, and the cytological characteristics of the cancer cells of the primary tumor and the CTCs were compared. The results are shown in FIGS. 9 and 10.

Specifically, as shown in FIG. 9, the visual pictures on the primary colorectal cancer and the recurrence of liver cancer of the patient and the histological findings on primary colorectal cancer were confirmed, and the CTCs were confirmed in the paraffin block sections prepared from the patient's blood collected in July 2012, according to the method of the present invention.

Additionally, as shown in FIG. 10, the CTCs observed in the patient's blood were subjected to the H & E staining and the CK immunohistochemical staining, and as a result, it was confirmed that a few cells showed negative findings to the CK staining.

These results suggest that a more sensitive detection can be performed b combining the tissue-specific markers already used in pathological diagnosis of metastatic cancers with uncertain primary site.

Accordingly, the method of preparing the paraffin blocks of the present invention is a method for the detection of CTCs present in the blood by collecting a blood sample. The method of the present invention is non-invasive and simple and thus it will be very useful for the diagnosis of cancer recurrence and prediction of prognosis, and will be able to provide a breakthrough in cancer treatment via analyses of the mechanisms of cancer occurrence, metastasis, and recurrence.

The invention claimed is:

1. A method of aggregating cells within the blood in a paraffin block comprising:
   (1) removing red blood cells from a blood sample obtained from a subject;
   (2) extracting the remaining cells within the blood from the blood sample;
   (3) mixing said remaining cells with a cell aggregating agent that comprises gelatin at a concentration from 5 mg/ml to 35 mg/ml, wherein the cell aggregating agent does not comprise fibronectin or laminin, to form a cell aggregate;
   (4) curing the cell aggregate by placing the cell aggregate at a temperature ranging from 2° C. to 5° C. for 15 minutes to 30 minutes to produce a cured cell aggregate product; and
   (5) treating the cured cell aggregate product sequentially with alcohol, xylene, and paraffin in an autopenetration process to produce a paraffin block with aggregated cells.

2. The method of claim 1, wherein removing the red blood cells in step (1) is performed using ficoll.

3. The method of claim 1, wherein in step (3), the cells and cell aggregating agent are mixed in a volume ratio of 1:1-1.5.

4. The method of claim 1, wherein the aggregating agent is mixed with the cells in step (3) having the following gelatin concentration ranges;
   (a) the concentration of the gelatin is 5 mg/mL to 15 mg/ml when the temperature is higher than or equal to 5° C. but lower than 15° C.;
   (b) the concentration of the gelatin is 15 mg/ml to 25 mg/ml when the temperature is higher than or equal to 15° C. but lower than 25° C.; or (c) the concentration of the gelatin is 25 mg/ml to 35 mg/ml when the temperature is higher than 25° C. but lower than 35° C.

5. The method of claim 1, wherein the paraffin block is used for histological, immunohistochemical, or molecular biological detection methods of circulating tumor cells.

6. The method of claim 1, wherein the cell aggregating agent in step (3) further comprises chondroitin sulfate, starch, or both chondroitin sulfate and starch.

* * * * *